United States Patent [19]
Bakker et al.

[11] Patent Number: 5,952,007
[45] Date of Patent: Sep. 14, 1999

[54] FAT REPLACER, ESPECIALLY FOR FOODS AND COSMETICS

[75] Inventors: Marinus Adriaan Bakker, Maassluis; Mettina Maria Koning, Berkel & Rodenrijs; Johannes Visser, Maassluis, all of Netherlands

[73] Assignee: Van den Bergh Foods Co., Lisle, Ill.

[21] Appl. No.: 08/629,453

[22] Filed: Apr. 10, 1996

Related U.S. Application Data

[63] Continuation of application No. 08/171,797, Dec. 22, 1993, abandoned.

[30] Foreign Application Priority Data

Dec. 23, 1992 [EP] European Pat. Off. .............. 92204075

[51] Int. Cl.⁶ ...................................................... A61K 9/52
[52] U.S. Cl. ........................ 424/489; 424/490; 424/491; 424/492; 424/493; 424/496; 424/499; 424/500; 424/501; 514/963; 514/951; 426/96
[58] Field of Search ..................................... 424/497, 401, 424/489, 490, 491, 492, 493, 496, 499, 500, 501; 514/963, 951; 426/96

[56] References Cited

U.S. PATENT DOCUMENTS

| | | | |
|---|---|---|---|
| 3,691,270 | 9/1972 | Charle et al. | 424/401 |
| 3,872,024 | 3/1975 | Hörger | 424/497 |
| 5,147,677 | 9/1992 | Ziegler | 426/614 |

FOREIGN PATENT DOCUMENTS

| | | |
|---|---|---|
| 273 823 | 12/1987 | European Pat. Off. . |
| 298 561 | 1/1989 | European Pat. Off. . |
| 340 035 | 4/1989 | European Pat. Off. . |
| 468 552 | 5/1991 | European Pat. Off. . |
| 27 01 361 | 10/1978 | Germany . |
| 60-112900 | 6/1985 | Japan . |
| 63-023736 | 2/1988 | Japan . |
| 1111440 | 4/1989 | Japan . |
| 93/19621 | 3/1993 | WIPO . |

OTHER PUBLICATIONS

Deasy, *Microencapsulation and Related Drug Process*, 1988, Marcel Decker, New York, Chapter 3, Coacervation—Phase Separation Procedures Using Aqueous Vehicles, pp. 61–81.

"Microencapsulation I. Phase Separation or Coacervation", by P. P. Madan from *Drug Development and Industrial Pharmacy*, 4(1), 1978, pp. 95–116.

*Primary Examiner*—Raj Bawa
*Attorney, Agent, or Firm*—Gerard J. McGowan, Jr.

[57] ABSTRACT

The use of complex coacervates of two or more biopolymer materials, preferably at least one of these being gelatin, as a fat-replacing ingredient. The complex coacervates may be used in foods and cosmetics and preferably are of substantially spherical or elliptical shape and have an average $D_{3,2}$ particle size, of from 0.2 to 100 microns.

7 Claims, No Drawings

FAT REPLACER, ESPECIALLY FOR FOODS AND COSMETICS

This is a continuation application of Ser. No. 08/171,797, filed Dec. 22, 1993 now abandoned.

TECHNICAL FIELD OF THE INVENTION

The present invention relates to fatty ingredients, in particular to fatty ingredients which can be used for the full or partial replacement of fat. Also the invention relates to products containing these ingredients.

BACKGROUND OF THE INVENTION

Over the last decade many non-triglyceride substances have been described as potential fat-replacers in food products. Examples thereof are waxes, e.g. jojoba oil and hydrogenated jojoba oil, polysiloxanes, acylated glycerides, polyalkoxyglycerolethers, dicarboxylic acid esters, polyol fatty acid polyesters and the epoxy extended derivatives thereof. Examples of disclosures of fat-replacers are e.g. 3,600,186, U.S. Pat. No. 4,005,195 and U.S. Pat. No. 4,005,196.

In particular effort has been directed towards the development of fat-replacement compositions which possess a smooth and oily taste, texture, mouthfeel and lubricity without resulting in an off-taste or malodour.

EP 355 908 discloses a fluid composition with a smooth fat-like consistency, which is obtained by cooling a polysaccharide liquid under shear.

EP 237 120 discloses fat-continuous food products with a reduced fat content by using a dispersed aqueous phase having a specific viscosity.

EP 298 561 relates to edible plastic dispersions of low fat content, comprising at least two condensed phases.

EP 340 035 relates to a method of producing a microfragmented fat-replacement composition by a complicated process involving the subjection of a complex dispersion of an ionic polysaccharide/protein complex to high shear.

The objects of the present invention are to provide a fat-replacement composition which can easily be prepared and which provides oily properties without having an off-taste or an undesired malodour.

Surprisingly it has been found that the above mentioned objects can be achieved by using a complex coacervate of two or more biopolymer materials. Preferably at least one of these biopolymer materials is gelatin.

Complex coacervation is a well-known phenomenon in colloid chemistry, an overview of coacervation techniques for encapsulation is for example provided by P. L. Madan c.s. in Drug Development and Industrial Pharmacy, 4(1), 95–116 (1978) and P. B. Deary in "Microencapsulation and drug processes", 1988 chapter 3. In general coacervation describes the phenomenon of salting out or phase separation of lyophilic colloids into liquid droplets rather than solid aggregates. Coacervation of a polymeric ingredient can be brought about in a number of different ways, for example a change in temperature, a change of pH, addition of a low molecular weight substance or addition of a second macromolecular substance. Two types of coacervation exist: simple coacervation and complex coacervation. In general, simple coacervation usually deals with systems containing only one polymeric ingredient, while complex coacervation deals with systems containing more than one polymeric ingredient.

EP 468 552 relates to fat substitutes comprising xanthan gum and one or more additional ingredients including other gums, proteins, salts, acidulants, alkaline agents and emulsifiers. The examples illustrate the formation of a complex between xanthan and milk protein under conditions whereunder both molecules carry a negative charge. No complex coacervates can be formed under these circumstances.

DE 2 701 361 relates to small gelatin droplets for fat replacement. The possibility of combining gelatin with other ingredients like protein is disclosed. Complex coacervates are neither disclosed or mentioned.

U.S. Pat. No. 5,147,677 relates to the manufacture of microparticulated protein for example by aqueous phase partitioning of egg white and gelatin. This phase partitioning leads to simple coacervation. Complex coacervates are not disclosed.

EP 273 823 relates to complex coacervates of gelatin and polysaccharide. The main application is for encapsulation; for example encapsulation of aromes or herbs. These encapsulates most likely are only used at very low levels (e.g. below 1%) in food products; fat-replacement is neither mentioned or suggested.

JP 63/023736 and J01/111440 discloses the production of microcapsules whereby the encapsulation is done by coacervation. Fat replacement or food products containing significant levels of coacervates are not disclosed.

SUMMARY OF THE INVENTION

Accordingly, the present invention relates to the use of complex coacervates of two or more biopolymer materials as a fat-replacing ingredient.

Also the invention relates to products containing the above described complex coacervates. In particular it has been found that the above fat-replacement can best be obtained if the level of complex coacervates is at least 1 wt % of the product. Suitable products are for example food products, e.g. spreads, dressings, creams, cheese, ice-cream, sauces, pates and confectionery products, and cosmetic products, for example lipsticks, creams, lotions etc.

Accordingly to a second aspect of the present invention there is provided a food product or cosmetic product comprising from 1–99.9 wt % of complex coacervates of two or more biopolymer materials.

Complex coacervates for use in accordance to the invention comprise at least two biopolymer materials. The biopolymer materials may for example be selected from the group of carbohydrates, proteins, gums, phospholipids etc.

Preferably at least one of the biopolymer materials is a protein. Most preferred is the use of gelatin as one of the biopolymer materials. Although applicants do not wish to be bound by any theory, it is believed that the presence of gelatin in the coacervates is particulary advantageous because this results in regularly shaped coacervate particles which may melt at a temperature between 25° C. and 40° C. and hence can provide a fatty consistency and mouthfeel.

Other advantages are the good keepability of the product and the non-acid taste even at relatively low pH values. Furthermore the complex coacervates of the invention have the advantage that they can easily be prepared, for example by phase separation without the use of substantial amount of synthetic ingredients and without the use of high shear or other complicated techniques like gas-atomization.

Complex coacervates of the invention comprise at least two biopolymer materials. The choice of the biopolymer materials should be such that complex coacervation may occur. Generally this will require that at the pH of preparation the polymer ingredients can be ionised in water, and whereby the electrical charge of one of the biopolymer materials is opposite to the electrical charge of the other biopolymer(s).

It is believed to be within the capability of a skilled person to select those combinations of polymer materials, their concentration and pH, which may result in the desired complex coacervate formation. Suitable biopolymers may for example be selected from the group of proteins, carbohydrates, gums, phospholipids etc. Preferred is the use of gelatin as one of the biopolymer materials.

Preferably two biopolymer materials are used. For example the following biopolymer combinations are considered particularly advantageous: acid gelatin and alkaline gelatin; gelatin and alginate; gelatin and pectin; gelatin and acacia gum; gelatin and lecithin; gelatin and carrageenan; gelatin and xanthan and gelatin and gellan gum. Other combinations include protein and protein, protein and phosphatide and protein and lipid complexes. A particularly preferred combination of biopolymer materials comprises gelatin and acacia gum, optionally in combination with a third biopolymer, for example pectin.

Preferably gelatin is used. The bloom strength of the gelatin is preferably from 50 to 350, more preferred 120 to 300, most preferred 200–280.

Particularly preferred is the use of two biopolymer materials in a weight ratio of 20:1 to 1:20, more preferred, 10:1 to 1:10, most preferred 5:1 to 1:5. If more than two biopolymer materials are used, the above ratios preferably apply to on the one hand the positively charged polymers and on the other hand the negatively charged biopolymers (at the pH of preparation of the product).

The complex coacervates of the invention may be prepared by any technique suitable for the preparation of complex coacervates. A preferred method of preparation involves the phase separation of the complex coacervates, possibly followed by a concentration step. A suitable separation process, involves for example the solubilisation of the biopolymer materials in water for example at slightly elevated temperature. If necessary, in order to allow complex formation the pH of the solution is brought at the required value. The solution is then optionally cooled to the desired temperature. A concentration step may for example be accomplished by filtration, (freeze) drying or centrifugation.

A particular preferred process involve the addition of 0.5–40 wt %, more preferred 1–20 wt %, most preferred 2–10 wt % of biopolymer materials to water of 30 to 100° C., more preferred 50 to 90° C., most preferred 60 to 80° C., possibly followed by bringing the pH to a value close to the isoelectric point of the coacervate (generally less than 2 pH units from the isoelectric point, more preferred less than 1 pH unit from the isoelectric point, most preferred from 0–0.5 pH unit from the isoelectric point) and cooling the mixture to a temperature of 0 to 30° C., more preferred 5 to 25° C., most preferred 10 to 20° C. The complex coacervate particles can then advantageously be isolated by conventional techniques, for example decanting followed by centrifuging, filtration or drying.

Preferably the preparation is carried out at low shear, for example shear rates are less than 25,000 reciprocal seconds, more preferred less than 1,000, most preferably the preparation is carried out under gentle stirring. Also preferably the process is carried out without the use of gas-atomizers; especially it is preferred that the high pressures as generally used in applying these techniques are preferably to be avoided. Preferably the pressure is less than 150 kPa, more preferred less than 50 kPa, most preferred the preparation is carried out at atmospheric pressure.

The resulting complex coacervate particles are generally of a substantially spherical or elliptical shape, although sometimes (being less preferred) under shear oblong particles may be formed. The average $(D_{3,2})$ particle size is preferably from 0.2 to 100 $\mu$m, more preferred 2.5 to 50 $\mu$m, most preferred 3 to 40 $\mu$m.

Preferably complex coacervates of the invention preferably have a melting point of between 10 and 90° C. e.g. 10–40° C. For use in some products, e.g. spreads, dressings, sauces etc, the higher end of the range is preferred, for example 25° C. to 40° C., more preferred 30° C. to 35° C., while for other products, e.g. ice-cream, skin cream, lipstick etc the melting point is preferably lower, for example from 15° C. to 25° C. Preferably the complex coacervates have a thermoreversible melting point. For certain product applications, e.g. processed cheese, the melting point is preferably high enough to allow the pasteurization of the product, without irreversibly destroying the complex coacervate particles.

The complex coacervate particles of the invention may optionally comprise further ingredients such as colouring, flavouring, preservatives, etc. The balance of the complex coacervate particles is generally water, which may be added as such or in another form e.g. in milk.

The resulting complex coacervate particles are further sometimes characterised by an electrophoretic mobility which is substantially zero. In this context, electrophoretic mobility may be measured by conventional techniques, for example by using a System 3000 electrokinetic analyzer ex Penkem or a Zetasizer 3c, ex Malvern.

As described above the complex coacervates of the invention, preferably are used at a level of 1 wt % or more in food products or cosmetics.

Examples of foodstuffs in which the complex coacervate particles may be used, are spreads, in particular zero- or extremely low fat spreads (which contain less than about 20% of fat), dressings, i.e. spoonable or pourable dressings e.g. dressings of the mayonnaise-type, dairy and non-dairy creams, toppings, processed cheese, pâtés, semi-hard cheese, sauces, sweet spreads, pastry-margarines, ice cream and coating materials e.g. couvertures for enrobing food products like ice-cream. Preferred food products are ready to eat food products. Also preferred are food products packed in portions of 1–5000 g, for example 10–1000 g, for example in tubs, bottles, wrappers, boxes etc.

Preferred cosmetic products are skin creams, moisturizer lotions, hair gels, deodorants, anti-perspirants, lipsticks etc.

The presence of complex coacervate particles in food products or cosmetics may be detected by any suitable technique.

Preferably the total level of complex coacervate particles in food products or cosmetic products of the invention is more than 1 wt % and less than 99.9 wt %, for example 2–99.9 wt %, more preferred 5–98 wt %, for example about 10 wt %, 20 wt %, 30 wt %, 40 wt %, 50 wt %, 60 wt %, 70 wt %, 80 wt %, 90 wt % or 95 wt %.

For preparing food-products or cosmetics containing the complex coacervate particles in accordance to the invention, it is generally preferred to prepare the complex coacervate particles separately and add this phase as an ingredient to the other ingredients of the product. Alternatively it is sometimes possible to prepare the complex coacervate particles in the presence of one or more other ingredients of the composition.

DETAILED DESCRIPTION OF THE INVENTION

The invention will be further illustrated by means of a number of specific embodiments: it will be evident that the scope of the invention is not limited to these specific embodiments.

I Dressings or Mayonnaise

A first embodiment of the present invention relates to dressings containing the above described complex coacervate particles.

Generally dressings or mayonnaise are oil in water emulsions. The oil phase of the emulsion generally is 0 to 80% by weight of the product. For non-fat reduced products the level of triglycerides is generally from 60–80%, more preferred from 65–75% by weight. For salad dressings the level of fat is generally from 10–60%, more preferred from 15 to 40%. Low or no-fat content dressings may for example contain triglyceride levels of 0, 5, 10 or 15% by weight.

Other fatty materials such as for example polyol fatty acids ester may be used as a replacement for part or all of the triglyceride materials.

The level of complex coacervate particles in the dressing will generally be from 10 to 80%, more preferred from 20 to 60%, most preferred from 40 to 50% by weight. Preferably the level of biopolymer materials is from 1 to 10%, most preferred, 2–8%, most preferred, 4 to 6% by weight, based on the weight of the dressing. If gelatin is used as one of the biopolymer materials, its level is preferably from 0.5–5 wt %, more preferred, 1 to 4%, most preferred 2–3%.

In addition to the above mentioned ingredients dressings in accordance to the present invention optionally may contain one or more of other ingredients which may suitably be incorporated into dressings and/or mayonnaise. Examples of these materials are emulsifiers, for example egg-yolk or derivatives thereof, stabilisers, acidifiers, bulking agents, flavours, colouring agents etc. The balance or the composition is water, which could advantageously be incorporated at levels of from 0.1–99.9%, more preferred 20–99%, most preferred 50 to 98% by weight.

As described above the complex coacervates for use in the mayonnaise of dressing are prepared separately before adding the other ingredients of the composition, or are formed in the presence of other ingredients.

During this process it is generally preferred that at some stage the ingredients are mixed under such conditions that the required emulsion structure can be formed. Such a mixing can usually take place under moderate shear.

II Spreads

Another preferred embodiment of the invention is the use of complex coacervate particles as described above, in spreads.

Spreads according to the embodiment generally contain from 0–80% by weight of edible triglyceride materials. Suitable edible triglyceride materials are for example disclosed Bailey's Industrial Oil and Fat Products, 1979. In spreads of non-reduced fat content (margarines), the level of triglyceride material will generally be from 60–80%, preferably from 70 to 79% by weight. In spreads of reduced fat content the level of triglycerides will generally be from 30–60%, more general from 35 to 45% by weight. In very low fat spreads the level of triglycerides will generally be from 0–40%, for example 30%, 25%, 20% or even 10% or about 0%. Other fatty materials, for example sucrose fatty acid polyesters may be used as a replacement for part or all of the triglyceride material.

Since the complex coacervates of the invention are especially suitable as a fat-replacer, it is preferred that the fat level of spreads of the invention is less than 40 wt %, more preferred are spreads having a fat content of 0–20 wt %, most preferred are spreads which are substantially free from fat, e.g. having a fat level of less than 5 wt %, 2 wt % or even about 0 wt %.

The level of the dry biopolymer materials in spreads is preferably from 0.1 to 15%, more preferred from 1–10%, most preferred from 2 to 8% by weight of the spread. The level of gelatin—if any—is preferably from 0.1–15 wt %, more preferred, 0.1 to 8%, most preferred 0.5–6%.

In addition to the above mentioned ingredients, spreads in accordance to the invention may optionally contain further ingredients suitable for use in spreads. Examples of these materials are gelling agents, sugar, EDTA, spices, salt, bulking agents, flavouring materials, colouring materials, proteins, acids etc. The balance of the composition is generally water, which may be incorporated at levels of up to 99.9% by weight, more general from 10 to 98%, preferably from 20 to 97% by weight. These percentages refer to the total water content of the product, including the water present in the complex coacervate phase.

Spreads of the invention preferably have a pH of 3–7, more preferred 3.5–6, most preferred 4–5.

Spreads according to the invention may be fat and/or water continuous. Given the preference for low fat spread products, water continuous products are generally preferred.

Again, in the preparation of spreads in accordance to the invention, the complex coacervate particles may either prepared before the addition of other ingredients, or the complex coacervates may be prepared while other ingredients of the composition are present.

III Whippable Products Such as Creams

Another preferred embodiment of the invention is the use of complex coacervate particles in whippable products, in particular whippable non-dairy creams, mousses, bavarois, etc.

Preferably the level of dry biopolymer materials in whippable dairy products is from 0.1 to 15% by weight, more preferred 1 to 10%, most preferred 2 to 8% by weight of the composition. The level of gelatin—if any—is preferably from 0.1–15 wt %, more preferred, 0.3 to 10%, most preferred 0.5–8%.

In addition to the above mentioned materials, whippable products in accordance to the invention may advantageously contain one or more other ingredients, for example proteins, sugar, emulsifiers, colorants, flavouring agents, fat (preferably vegetable fat), skimmed milk ingredients etc. For example the fat level may be from 0 to 80%, more preferred 0–40%, for example about 5%, 15% or 30%. Especially preferred are whippable product of reduced or zero fat content, e.g. having a fat level of less than 20 wt %, more preferred less than 10 wt %, most preferred from 0 to 5 wt %. The balance of the composition is preferably water.

As described above the complex coacervate particles are prepared before mixing the remaining ingredients or may be formed in the presence of one or more other ingredients of the composition.

IV Ice Cream or Other Frozen Desserts

A further advantageous embodiment of the present invention relates to the use of complex coacervate particles in frozen desserts.

Problems often encountered while using conventional fat-replacers in frozen desserts are off-flavours and difficulties in suitably controlling the structure and eating characteristics. It has been found that while using the complex coacervate particles as described above, frozen desserts can be obtained having the structure and sensoric properties of ice cream but a lesser caloric content. Also fat-free ice-cream like products can be obtained.

Furthermore the use of complex coacervates, especially gelatin containing complex coacervates, can provide frozen desserts having improved melt-down properties.

Although by using the complex coacervates an ice-cream impression can be achieved without any fat, it may for some flavours be convenient to use a relative small amount of fat or monoglycerides (e.g. up to 2 to 3% by weight, preferably 0.5 to 1% by weight) for improving the flavour release. Needless to say that the calorific content increases by this addition.

Preferred frozen dessert compositions contain from 0.1 to 10% of dry biopolymer materials, more preferred from 0.3 to 8%, most preferred from 0.5 to 6% by weight. Preferably the level of gelatin—if any—is from 0.1 to 10%, more preferred from 0.2 to 6%, most preferred from 0.5 to 6% by weight.

In addition to the complex coacervates, frozen desserts of the present invention may contain all conventional ingredients suitable for incorporation therein. For example, frozen desserts according to the present invention will usually contain one or more ingredients for improving the sweetness thereof. Preferably sugar is used as the sweetening material. If sugar is used as sweetening agent, the level thereof is preferably from 5–40%, more preferred 10–20%. If other sweetener materials such as for example aspartame (trademark) are used, the level of these materials is chosen such that the sweetness of the product resembles that of a product having the above mentioned sugar contents. Use of artificial sweetener materials may further require the use of one or more bulking agents, for example hydrogenated starch materials.

Furthermore frozen desserts according to the invention preferably contain milk solids non fat (MSNF) at levels of 1–20%, more preferred 6–14% by weight. Additionally frozen desserts may advantageously contain low levels of emulsifier and/or stabilising agents, for example at a level of 0 to 0.5%, more preferred 0.2 to 0.4% by weight. Optionally further ingredients suitable for incorporation in frozen desserts may be used, for example fruit, flavours, colouring agents, chocolate, nuts, preservatives and freezing point depressants. Generally the balance of the composition will be water.

Frozen desserts according to the invention may be prepared by any conventional method for the preparation of ice-cream and the like. The complex coacervates may either be prepared separately or in the presence of other ingredients.

V Cheese

Another preferred embodiment of the invention relates to the use of complex coacervate particles in cheese products, for example processed cheese or semi-hard cheese.

Cheese products in general often contain dispersed droplets of fat dispersed in a matrix, which is often structured by casein. For the purpose of the present invention the complex coacervate particles may be used for replacing part or all of the dispersed phase, but also possible is that the coacervate particles used as a replacement for all or part of the cheese matrix. In both cases, the coacervate particles will be present as discrete spherical particles.

Preferably the level of biopolymer materials in the cheese milk will be from 0.1 to 10% by weight of the composition, more preferred 0.2 to 5%, most preferred 0.5 to 3%. Preferably the level of gelatin—if any—is from 0.01 to 2%, more preferred 0.1 to 0.4%.

In addition to the complex coacervate particles, cheese products of the invention may advantageously contain all types of ingredients which can be present in cheese, products. Examples of these ingredients are milk protein (preferably present at a level of 0–15%, more preferred 0.5 to 10%), fat (preferably present at levels from 0–45%, more preferred 1–30%; other fatty materials such as for example polyol fatty acid esters can replace all or part of the fat), electrolytes (for example $CaCl_2$ and/or NaCl at levels of 0 to 5%, more preferred 1–4%), rennet or rennin (for example at a level of 0.005 to 2%, more preferred 0.01–0.5%), flavours, colouring agents, emulsifiers, stabilisers, preservatives, pH adjusting agents etc. The balance of the product is generally water which may be present at levels of for example 0–99.5%, more preferred 5–80%, more preferred 30–75% by weight).

The cheese products according to the present invention range from soft cheeses to hard cheeses of various types such as semi hard cheeses (such as Gouda, Edam, Tilsit, Limburg. Lancashire etc), hard cheeses (for example Cheddar, Gruyere, Parmesan), external mould cheeses (e.g. Camembert and Brie), internal moulded cheeses (e.g. Roquefort, Gorgonzola etc), processed cheeses and soft cheeses (cottage cheese, cream cheese, Neufchatel etc.).

The cheese products of the invention may be prepared by any suitable process for the preparation of cheeses. Although this is dependent on the type of cheese, generally the following stages may be present: (1) mixing the ingredients into milk at a temperature below the melting point of the coacervate particles; (2) After cooling addition of a starter culture, cutting of the curd, moulding and eventual salting; and (3) ripening. As indicated above the complex coacervates may be formed separately or may be formed "in-situ". If the cheese preparation method requires the heating of the product above the melting point of the complex coacervate particles, it may be preferred to add the complex coacervates after the heating step, such that melting of the particles during preparation can be avoided.

VI Other Food Products

Other food products in accordance to the invention which could advantageously contain edible complex coacervates, involve other edible emulsified systems, sauces, sweet spreads, bavarois, liquid and semi-liquid dairy products, bakery cream, pates, toppings, coating materials like couvertures for ice-cream etc.

EXAMPLE 1

A complex coacervate (Sample A) of gelatin and acacia gum was prepared by mixing a 2% solution of Gelatin SG-720-N ex Extraco Geltec, Sweden (isoelectric point 8.2) and a 2% solution of Gum arabic, ex Merck, Darmstadt, Germany. The ingredients in dried form were dissolved in water of 45° C. followed by adjusting the pH to 5.5 for complete solubilization. After mixing and the addition of 0.1% K-sorbate to prolong the shelflife of the final product, the pH of the solution was dropped to 4.5 under stirring using 1N HCl, whereupon the coacervate particles are formed. The coacervate particles are solidified by cooling to room temperature. After overnight storage at 5° C. to promote phase separation, the particles are harvested by decanting and filtering over a Buchner funnel.

The resulting coacervate particles had a dry matter content of 12% and were of spherical shape and had an average $D_{3,2}$ particle size as measured in a Helos Sympatec particle size analyser of 11.3 micrometer. The melting point of the particles was about 31.5° C. The taste was bland, without a noticeable acid impression. The particles provided a fatty feel when rubbed between the fingers.

EXAMPLE II

Sample B:

Example I was repeated by using Pectin, type RS 150 SAG, ex Pomosin, Germany instead of acacia gum. The final pH of the system was 3.75. The resulting particles are spherical and have an average $D_{3,2}$ particle size of 7 micrometer. The melting temperature of the particles was approximately 70° C., the taste was bland, without a noticeable acid impression.

Sample C:

Example I was repeated by using a 1:1:0.1 mixture of gelatin, acacia gum (as in Sample A) and pectin (as in Sample B) as biopolymer ingredients. The level of the main components was 1 wt %. The resulting complex coacervate particles were spherical and had an average particle size $D_{3,2}$ of 8 micrometer. The melting point of the particles was approximately 31.5° C.

Sample D:

Example I was repeated by using Gelatin type oooo ex Lijm-en Gelatine Fabriek, Delft, Netherlands (isoelectric point 5.5) instead of Gelatin SG 720 N. The final pH was chosen at 3.75. The particles had an avearge size $D_{3,2}$ of 21.2 micrometer.

Sample E:

Example I was repeated by using Gelatin type oooo ex Lijm-en Gelatine Fabriek, Delft, Netherlands (isoelectric point 5.5) instead of acacia gum. The final pH was 3.75.

Sample F:

Example I was repeated by using sodium caseinate ex DMV-Campina, Veghel, Netherlands, instead of acacia gum. The final pH was 5.5. The particle size as measured by light microscopy was approximately 25 micrometer.

Sample G:

Example I was repeated by using a whey protein isolate, type Hyprol 8100, ex Quest, Naarden, Netherlands, instead of gelatin. The final pH was 3.75. The particle size of the coacervate particles as measured by light microscopy was approximately 25 micrometer.

Sample H:

Example I was repeated by mixing the components in dry form in water at a 2 wt % level, using acacia gum, type Ferwogum S/D Kordofan First Grade SF, ex Ferdiwo BV., Amstelveen, Netherlands, at 50° C. under stirring at 300 rpm while adjusting the pH to 3.75, followed by cooling to 15° C. The complex coacervate particles were separated from the solution by centrifugation at 1000 g, followed by decanting. The resulting particles were of spherical shape and had an average $D_{3,2}$ particles size of 25 micrometer. The melting point was about 31.5° C.

Sample J:

Sample G was repeated with the additional step of freeze drying the centrifuged mass to give a free-flowing powder. Upon dissolving the powder in water the original coacervate particles were restored.

EXAMPLE 3

A 40% fat dressing was prepared by low shear mixing in a Kenwood mixer, type Chef, of a commercial mayonnaise (80% fat) with the same amount of the coacervate particles at room temperature. The following ingredients were used:

coacervate particles (Example A) 50%
commercial mayonnaise (ex Calvé, Delft, the Netherlands) 50%

The Calvé product is a normal mayonnaise, available on the Dutch market. It is an O/W emulsion, containing 80% oil, with egg yolk as emulsifier. A very acceptable product with proper consistency (spoonable), fatty impression and organoleptical properties was obtained.

EXAMPLE 5

A nearly zero % fat mayonnaise was prepared using the following ingredients:

|  | wt % |
|---|---|
| water | balance |
| egg yolk | 4.13 |
| sugar, castor | 6.97 |
| vinegar 12% | 4.03 |
| NaCl | 1.00 |
| mustard, DV-15 | 1.00 |
| β-carotene 1% (CWS) | 0.03 |
| potassium sorbate | 0.10 |
| coacervate particles (Sample J) | 10.66 |

After weighing the individual ingredients, 1 l of the premix was prepared by disolving the ingredients (except for the coacervate particles) in water. The complex coacervate phase is then mixed in by hand and the product is stored overnight at 5° C. The pH of the product is 4.04.

The Stevens value of the product was 74 g, as measured with a standard mayonnaise gauze, the viscosity of the product was 6.7 Pa.s, as measured with the Haake VT-02 viscometer (rotor nr. 1). The product had an acceptable mouthfeel.

EXAMPLE 6

A 40% fat spread was prepared by low shear mixing of a commercial margarine containing 80% fat with the same amount of the coacervate phase (Example A) at room temperature. The following ingredients were used:

| coacervate particles (Example A) | 50% |
|---|---|
| commercial margarine (ex. Van den Bergh Foods, Rotterdam, Netherlands) | 50% |

The margarine and the coacervate phase were mixed in a simple household mixer at room temperature till a homogeneous mixture was obtained. The product was then cooled to 5° C. and packed in a plastic tub. After overnight storage a spreadable product was obtained. On inspection the product had the appearance of an edible fatty spread both when static and when spread onto bread. There was no evidence of loose moisture, even after further prolonged storage. The product was fat continuous, as could be shown by light microscopy and electrical conductivity.

The commercial margarine was Becel, a high PUFA product, available on the Dutch market, containing 80% fat, but also other margarines and high fat spreads may be used instead.

EXAMPLE 7

A 5% fat spread was prepared using the following ingredients

|  | wt % |
|---|---|
| Paselli SA2 | 11.30 |
| sweet cream buttermilk powder | 2.00 |
| NaCl | 1.00 |
| β-carotene 1% (CWS) | 0.05 |
| potassium sorbate | 0.13 |
| TAG(SF-oil) | 5.00 |
| coacervate particles (sample A) | 40.27 |
| water | balance |

After dissolving the Paselli in water at 90° C. using an ultraturrax, the other (except for the coacervate particles) ingredients are added at 65° C. After cooling to 25° C., the coacervate particless are added The product is then further cooled down under slow stirring till 10° C. and homogenized in a Manton-Gaulin at 150/50 bar. The product is filled into tubs and stored at 5° C. The product had a pH of 4.84 and had an acceptable spread-like character.

EXAMPLE 8

A spread was prepared using the following ingredients

|  | wt % |
|---|---|
| Hymono 8806-1156 | 3.5% |
| Admul datem 1935 | 0.35 |
| β-carotene (CWS) | 0.07 |
| xanthan gum | 0.60 |
| LBG | 0.05 |
| TiO$_2$ | 0.20 |
| NaCl | 1.40 |
| potassium sorbate | 0.12 |
| water | balance |

A dry mix of NaCl, potassium sorbate, Xanthan, TiO$_2$, β-carotene and LBG is added to water in the given concentrations at 90° C. and cooled to 58° C., when the Admul Datem and the Hymono are introduced. The mixture thus obtained is then cooled in a Moltomat under vacuum while mildly stirring to a temperature of 18° C.

80 parts of mixture is combined with 20 parts of the coacervate phase of example A and mixed till a homogeneous mass is obtained. The product is next homogenized in a Manton Gaulin at 100/50 bar, filled in tubs and stored at 5° C.

The spread thus obtained had a good texture, was homogeneous, and had a good spreadability.

EXAMPLE 9

A mixture containing the following ingredients was prepared in a simple mixer at room temperature.

|  | g. |
|---|---|
| coacervate phase (Example A) | 750 |
| guar gum | 15 |
| MD20 | 502.5 |
| LBG | 7.5 |
| SMP | 495 |
| whey powder | 127.5 |
| sucrose | 870 |
| water | 4732.5 |

The temperature was reduced to 5° C., and the mixture was homogenized using a single stage Rannie homogenizer at a pressure of 150–180 . 10$^5$ Pa, 0.05% vanilla flavour was added and the mixture was allowed to age for 24 hours. Thereafter the mixture was whipped to 100% overrun while cooling in a usual continuous ice cream freezer (Hoyer MF50) to −5° C. The resulting creamy frozen dessert could be eaten as such or be stored after cooling down to usual storage temperatures, e.g. −25° C.

The melt-down properties were not too different from usual ice cream, but markedly better than usual fat-free or low fat frozen desserts.

EXAMPLE 10

A low fat Gouda type cheese was prepared from a cheese milk comprising 98% pasteurized low fat milk (1.3% fat, 3.5% protein) and 1% coacervate particles (Example A), having a melting point of 31.5° C. The coacervate particles were dispersed in the milk using a hand held electric stirrer.

To 300 liters of this cheese milk the following composition was added:

| 57 g | CaCl$_2$ |
|---|---|
| 45 g | KNO$_3$ |
| 5 ml | single strength Annatto colour |
| 2.1 l | 'BOS' culture |
| 90 ml | calf rennet |

After 45 minutes clotting at 29° C. the curd was cut to cubes of approx. 5 mm and after 1 min sedimentation 155 l whey was removed. Washing water (114 l, 30° C.) was added and after 28 min holding time the curd was pressed into forms. After removal of the whey the (5 kg) cheese blocks were pressed for 3 h from 0.3 to 1.8 bar. Brining was carried out in 18 Baume brine for 18 h. The final pH of the unripened cheese was 5.2.

After normal ripening the resulting low fat cheese (20% fat on dry matter) had satisfactory consistency, texture and taste.

EXAMPLE 11

Complex coacervates were prepared as in Example I.

Mayonnaise products of the compositions as indicated in the table were made.

The method of preparation was:

a) Mix acetic acid, spiced vinegar and tap water b) Add β-carotene, K-sorbate, titanium dioxide, NaCl and 50% of the sugar content. Stir the mixture.

c) Mix guar with the remaining part of the sugar and add this mixture to the complex coacervate. Stir the mixture.

d) Add slowly the mixture obtained from c) to the mixture obtained in b) under stirring with a Kenwood mixer.

The resulting products had a good melting behaviour. When compared to a reference product (Die Leichte Belvita) the taste of products of the invention was significantly more creamy. No dry after-taste was observed.

TABLE

| Products (wt %) | example 11 | | | | | | |
| --- | --- | --- | --- | --- | --- | --- | --- |
| | A | B | C | D | E | F | G |
| Composition | | | | | | | |
| Sugar | 14.00 | 14.00 | 14.00 | 14.00 | 14.00 | 14.00 | 14.00 |
| NaCL | 1.90 | 1.90 | 1.90 | 1.90 | 1.90 | 1.90 | 1.90 |
| Acetic acid (50%) | 0.90 | 0.90 | 0.90 | 0.90 | 0.90 | 0.90 | 0.90 |
| Spiced vinegar (10%) ex. Calve' | 3.00 | 3.00 | 3.00 | 3.00 | 3.00 | 3.00 | 3.00 |
| β-carotene (1%) water soluble | | | | | | | |
| K-sorbate | 0.10 | 0.10 | 0.10 | 0.10 | 0.10 | 0.10 | 0.10 |
| Titanium dioxid (40% dispersion) | 0.50 | 0.50 | 0.50 | 0.50 | 0.50 | 0.50 | 0.50 |
| Guar | 0.20 | 0.20 | | | | | |
| Tap water | 24.39 | 39.39 | 29.59 | 24.59 | 19.59 | 9.59 | 9.59 |
| Total | 100.00 | 100.00 | 100.00 | 100.00 | 100.00 | 100.00 | 100.00 |
| pH | 3.75 | 3.75 | 3.75 | 3.75 | 3.75 | 3.75 | 3.75 |

Table, example 11

We claim:

1. A method for the preparation of homogeneous complex coacervate particles for use as a fat-replacing ingredient in a product, the total level of complex coacervate particles in said product being more than 1 wt. % and less than 99.9 wt. % said method comprising performing sequentially the following steps:

(a) solubilizing two or more biopolymers selected from the group consisting of carbohydrates, proteins, gums and phospholipids in water having a temperature of from 30 to 100° C.;

(b) optionally bringing the pH to a value close to the isoelectric point of the coacervate;

(c) cooling the mixture to a temperature of from 0 to 30° C.;

(d) isolating the complex coacervate; and (e) optionally concentrating the coacervate;

wherein said method is conducted at a pressure below 150 kPa, and with a shear rate of less than 25,000 reciprocal seconds, no use being made of a gas atomizer, the complex coacervate particles prepared being of substantially spherical or elliptical shape and having an average D3,2 particle size of from 0.2 to 100 μm.

2. The method in accordance with claim 1 wherein the biopolymers are selected from the group consisting of the following combinations; acid gelatin and alkaline gelatin; gelatin and alginate; gelatin and pectin; gelatin and acacia gum; gelatin and lecithin; gelatin and carrageenen; gelatin and xanthan; gelatin, acacia gum and pectin; and gelatin and gellan gum.

3. The method according to claim 1, said method comprising;

(a) mixing a 2% solution of gelatin and a 2% solution of acacia gum, said solutions being prepared by dissolving dried ingredients in water at a temperature of 45° C. followed by adjusting the pH to 5.5 for complete solubilization;

(b) adjusting the pH of the solution to 0 to 0.5 pH units from the isoelectric point to form a complex coacervate;

(c) cooling the mixture to room temperature; and (d) isolation of the formed complex coacervate.

4. The method according to claim 1, said method comprising:

(a) mixing a 2% solution of gelatin and a 2% solution of pectin, said solutions being prepared by dissolving dried ingredients in water at a temperature of 45° C. followed by adjusting the pH to 5.5 for complete solubilization;

(b) adjusting the pH of the solution to 0 to 0.5 pH units from the isoelectric point to form a complex coacervate;

(c) cooling the mixture to room temperature; and (d) isolation of the formed complex coacervate.

5. The method according to claim 1, said method comprising:

(a) mixing a 1% solution of gelatin and a 1% solution of acacia gum and a 0.1% solution of pectin, said solutions being prepared by dissolving dried ingredients in water at a temperature of 45° C. followed by adjusting the pH to 5.5 for complete solubilization;

(b) adjusting the pH of the solution to 0 to 0.5 pH units from the isoelectric point to form a complex coacervate;

(c) cooling the mixture to room temperature; and (d) isolation of the formed complex coacervate.

6. The method in accordance with claim 1, wherein the product is selected from the group consisting of food products and cosmetic products.

7. The method according to claim 1, wherein at least one of the biopolymers is gelatin.

* * * * *